United States Patent
Hsieh

(10) Patent No.: US 7,347,925 B2
(45) Date of Patent: Mar. 25, 2008

(54) BIOSENSOR FOR MONITORING AN ANALYTE CONTENT WITH A PARTIAL VOLTAGE GENERATED THEREFROM

(75) Inventor: Jun-Wei Hsieh, Hsin-Chu (TW)

(73) Assignee: Transpacific IP, Ltd., Taipei (TW)

( * ) Notice: Subject to any disclaimer, the term of this patent is extended or adjusted under 35 U.S.C. 154(b) by 674 days.

(21) Appl. No.: 10/609,617

(22) Filed: Jul. 1, 2003

(65) Prior Publication Data
US 2005/0000806 A1 Jan. 6, 2005

(51) Int. Cl.
*G01N 27/327* (2006.01)
*G01N 27/333* (2006.01)

(52) U.S. Cl. .............. 205/777.5; 205/792; 204/403.01; 204/403.14; 204/416

(58) Field of Classification Search .............................. 204/403.01–403.15, 406, 416–419; 205/777.5, 205/778, 792
See application file for complete search history.

(56) References Cited

U.S. PATENT DOCUMENTS

| | | | | |
|---|---|---|---|---|
| 3,539,455 | A * | 11/1970 | Clark, Jr. ..................... | 205/778 |
| 4,514,276 | A * | 4/1985 | Covington et al. ......... | 257/414 |
| 4,767,994 | A * | 8/1988 | Hopkins et al. ............. | 324/438 |
| 4,798,705 | A * | 1/1989 | Jakubowicz et al. .......... | 422/63 |
| 5,573,649 | A * | 11/1996 | Sugama et al. ........ | 204/403.06 |
| 5,876,577 | A * | 3/1999 | McAleer et al. ......... | 205/777.5 |
| 6,349,230 | B1 | 2/2002 | Kawanaka ................... | 600/347 |
| 6,706,038 | B2 * | 3/2004 | Francischelli et al. ........ | 606/34 |

FOREIGN PATENT DOCUMENTS

DE 2200119 A * 12/1973
DE 2200119 C3 * 9/1977

OTHER PUBLICATIONS

Derwent abstract for DE 2200119 A (Jul. 12, 1973).*
English language translation of Siemens (DE 220119 A), patent issued Sep. 29, 1977.*
English language translation of Siemens (DE 220119 C3), application publically available Jul. 12, 1973.*

* cited by examiner

Primary Examiner—Alex Noguerola
(74) Attorney, Agent, or Firm—Stolowitz Ford Cowger LLP

(57) ABSTRACT

A biosensor for monitoring an analyte content with a partial voltage generated therefrom is provided. The present biosensor includes a chip having a resistance $R_s$, a power source, and a microprocessor. The power source is used for supplying an applied voltage on the chip. The chip generates a time-dependent response current in response to a content of an analyte of a specimen applied thereon upon supplying the applied voltage on the chip. The microprocessor receives a time-dependent partial voltage caused from the chip due to the time-dependent response current, and determines the content of the analyte in accordance with the time-dependent partial voltage. The present biosensor is provided with fewer elements than a conventional one. A purpose of cost down is thus obtained.

40 Claims, 4 Drawing Sheets

BIOSENSOR FOR MONITORING AN ANALYTE CONTENT WITH A PARTIAL VOLTAGE GENERATED THEREFROM

BACKGROUND OF THE INVENTION

1. Field of the Invention

The present invention relates to a biosensor, and more particularly to a biosensor for monitoring an analyte content with a partial voltage generated therefrom.

2. Description of the Prior Art

In recent years, various kinds of biosensors utilizing a specific catalytic action of enzymes to be used for clinical purposes have been developed. A valuable use of such biosensors may be made in the area of diabetes treatment where it is vital for patients to keep their blood glucose concentration ("blood sugar level" below) within a normal range. For an inpatient, the blood sugar level can be kept normal under the supervision of the doctor. For an outpatient, self-control of the blood sugar level is an important factor for treatment in lack of doctor's direct supervision.

Self-regulation of blood sugar levels is achieved through a diet, exercise and medication. These treatments may often be simultaneously employed under the supervision of the doctor. It has been found that self-regulation works more effectively when the patient himself is able to check whether or not his blood sugar level is within the normal range.

Recently, blood sugar level measuring instruments have been used for self-checking of blood sugar levels. For example, U.S. Pat. No. 6,349,230 provides a blood sugar measuring instrument, as shown in FIG. 1, which mainly includes a main detecting unit 10 and a chip 12 for blood sugar measurement. As shown in FIG. 2, the chip 12 includes a strip-like substrate 122 provided in its front portion with an electrode section 1221. The electrode section 1221 is covered by a reaction layer 124, a spacer 126 and a cover sheet 128. The electrode section 1221 is provided with an operational terminal 1222 and a counterpart terminal 1224 surrounding the operational terminal 1222. The operational terminal 1222 and the counterpart terminal 1224 are electrically connected to lead terminals 1226 and 1228, respectively, which are formed on a base end portion of the strip-like substrate 122. The reaction layer 124, which covers the electrode section 1221, contains potassium ferricyanide and an oxidase such as glucose oxidase.

The blood sugar measuring instruments may be used in the following manner. A patient pricks his or her own skin with e.g. a lancet for drawing a small quantity of blood. Then, the blood may be deposited at the tip of the chip 12 plugged into the main detecting unit 1. The blood is partially sucked into the reaction layer 124 by capillary action. The reaction layer 124 disposed above the electrode section 1221, is dissolved by the blood, which starts an enzyme reaction, as the following formula:

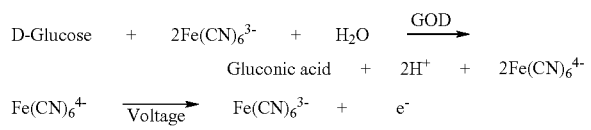

Potassium ferrocyanide is produced in an amount corresponding to the glucose concentration. After a certain period of time, a predetermined voltage $V_{ref}$ is applied on the chip 12 to electrochemically oxidize potassium ferrocyanide to release electrons. A response current is generated and passes through the operational terminal 1222. The response current is proportional to the concentration of potassium ferrocyanide produced by the enzyme reaction or to the concentration of the glucose. Therefore, the blood sugar level may be determined by measuring the response current.

FIG. 3 is a schematic diagram of a control circuit of the blood sugar measuring instrument of FIG. 1, in which the electrode section 1221 of the chip 12 can be regarded as a resistor $R_s$. The voltage $V_{ref}$ to be applied can be provided by a battery. The response current I generated by the chip 12 decays as time progresses to form a time-dependent discharge curve corresponding to the glucose concentration of the blood. Moreover, the response current I of each sampling time of the time-dependent discharge curve is converted to an output voltage $V_{out}$ by a current/voltage converter 30 formed of an operational amplifier 310 having an amplification resistance $R_f$. As a consequence, the response currents I decaying as time progresses form a voltage-time discharge curve. Each voltage of each sampling time of the voltage-time discharge curve is converted to a set of digital signals by an analog to digital converter 32. A microprocessor 34 reads the digital signals output from the analog to digital converter 32, and calculates the glucose concentration of the blood in accordance with the digital signals. A reading of the glucose concentration is displayed on a display such as a liquid crystal display (LCD) 36.

The conventional blood sugar measuring instrument utilizes the operational amplifier as the current/voltage converter 30. The control circuit of the conventional blood sugar measuring instrument is more complicated and power-consuming. Moreover, the operational amplifier 310 generates static current and dark current when the conventional blood sugar measuring instrument is in standby, resulting in the shortening of the use time of the battery. It is very inconvenient for a patient to change a battery constantly. The electronic parts used in the control circuit of the conventional blood sugar measuring instrument are also costly. The manufacturing cost of the conventional blood sugar measuring instrument can not be reduced.

Accordingly, it is an intention of the current disclosure to provide an improved blood sugar measuring instrument, which can alleviate the above drawbacks.

SUMMARY OF THE INVENTION

It is one objective of the present invention to provide a biosensor for monitoring an analyte content with a partial voltage generated therefrom, which is provided with fewer elements than a conventional one in order to reduce costs.

It is another objective of the present invention to provide a biosensor for monitoring an analyte content with a partial voltage generated therefrom, in which an operational amplifier, used in a conventional one, is omitted, and the present biosensor would not generate static current and dark current when in standby. The use time of a battery for supplying power to the present biosensor is extended.

It is a further objective of the present invention to provide a biosensor for monitoring an analyte content with a partial voltage generated therefrom, comprising fewer electronic parts than a conventional one, and the power consumption can be reduced.

It is still a further objective of the present invention to provide a biosensor for monitoring an analyte content with a partial voltage generated therefrom, comprising fewer electronic parts than a conventional one. The interference of the electronic parts is eliminated and the discrimination of the content of the analyte is improved.

In order to achieve the above objectives of this invention, the present invention provides a biosensor for monitoring an analyte with a partial voltage generated therefrom. The biosensor includes a chip having a resistance $R_s$, a power source, and a microprocessor. The power source is used for supplying an applied voltage on the chip. The chip generates a time-dependent response current in response to a content of an analyte of a specimen applied thereon upon supplying the applied voltage on the chip. The microprocessor receives a time-dependent partial voltage caused from the chip due to the time-dependent response current, and determines the content of the analyte in accordance with the time-dependent partial voltage.

The present biosensor is provided with fewer electronic parts than a conventional one. Hence, both of the manufacturing cost and power consumption can be reduced. Furthermore, the present invention monitors the content of the analyte of the specimen directly depending on a time-dependent partial voltage caused from the chip due to the time-dependent response current. The interference of the electronic parts is eliminated, and the discrimination of the content of the analyte is improved.

BRIEF DESCRIPTION OF THE DRAWINGS

The objectives and features of the present invention as well as advantages thereof will become apparent from the following detailed description, considered in conjunction with the accompanying drawings.

DESCRIPTION OF THE PREFERRED EMBODIMENTS

Figure 1:
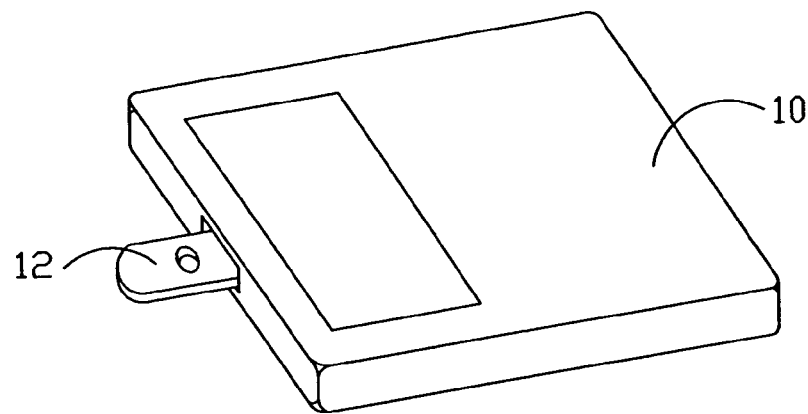
FIG. 1 is a schematic perspective view of a conventional blood sugar measuring instrument.
Figure 2:
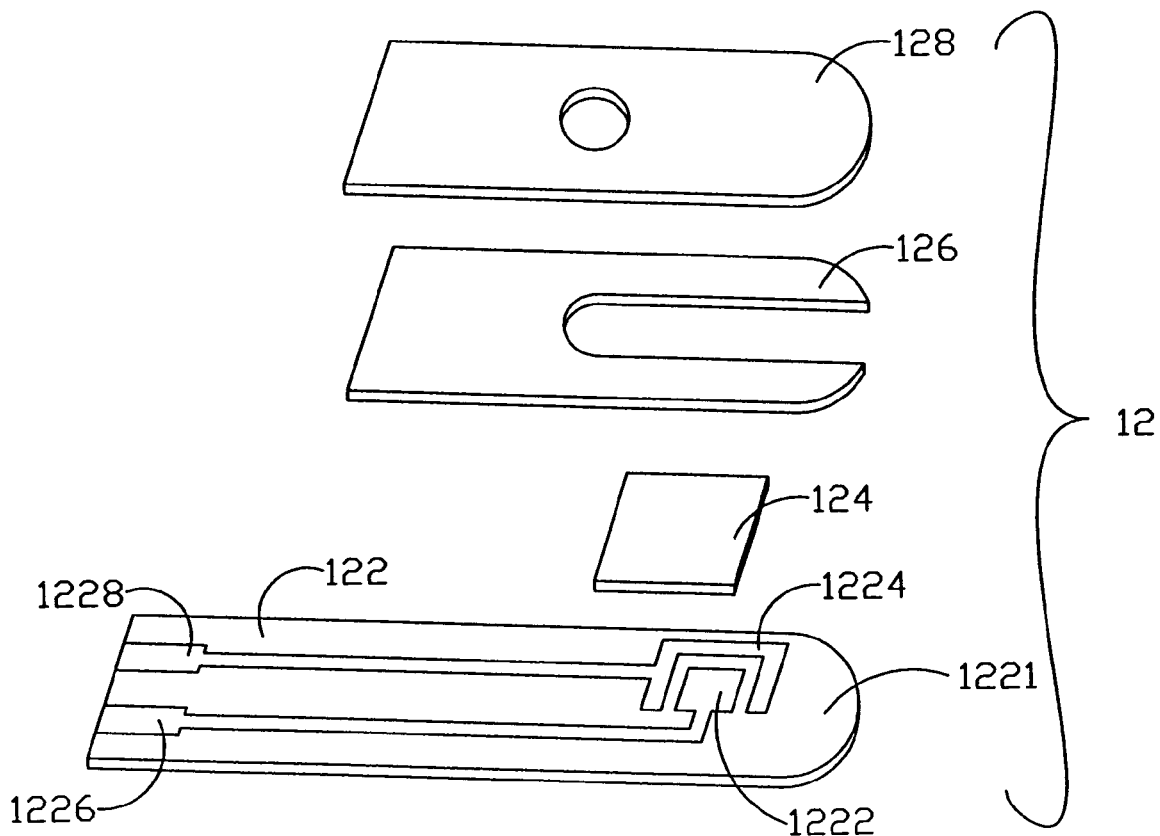
FIG. 2 is an exploded view of a chip of the conventional blood sugar measuring instrument of FIG. 1.
Figure 3:
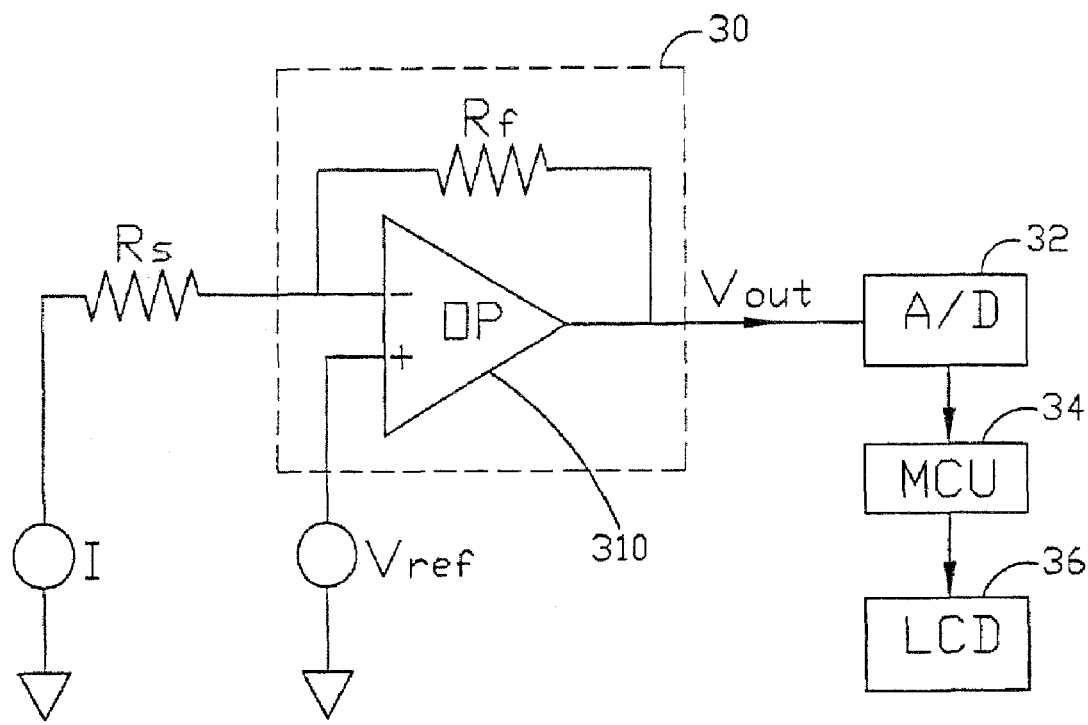
FIG. 3 is a schematic diagram of a control circuit of the conventional blood sugar measuring instrument of FIG. 1.

The principle of the present invention for monitoring a content of an analyte of the specimen is the same with that of the conventional biosensor of FIG. 1. The specimen is applied on the chip having been plugged into the main detecting unit of the biosensor of the present invention. And, the content of the analyte to be detected present in the specimen is determined in accordance with a result of an enzyme-catalytic reaction between the analyte and the enzyme of the chip. Therefore, the analyte of the specimen to be detected depends on the type of the enzyme of the chip. For example, when the chip contains glucose oxidase, the biosensor can be used to monitor a glucose concentration of a blood sample. When the chip contains lactate oxidase, the biosensor can be used to monitor a concentration of lactic acid of saliva. For example, when monitoring the glucose concentration of the blood sample, the blood sample is applied on the chip of the present biosensor, the glucose of the blood sample and potassium ferricyanide proceed an electrochemical reaction under catalysis of the glucose oxidase, producing potassium ferrocyanide in an amount proportional to the glucose concentration. Hence, after a period of time that the blood sample has been applied on the chip, i.e. the enzyme-catalytic reaction completes, a power supply applies an applied voltage on the chip in order for the chip generating a response current in response to the blood glucose concentration. That is, the applied voltage makes potassium ferrocyanide in the amount proportional to the glucose concentration proceeding oxidation to release electrons so as to generate the response current.

Figure 4:
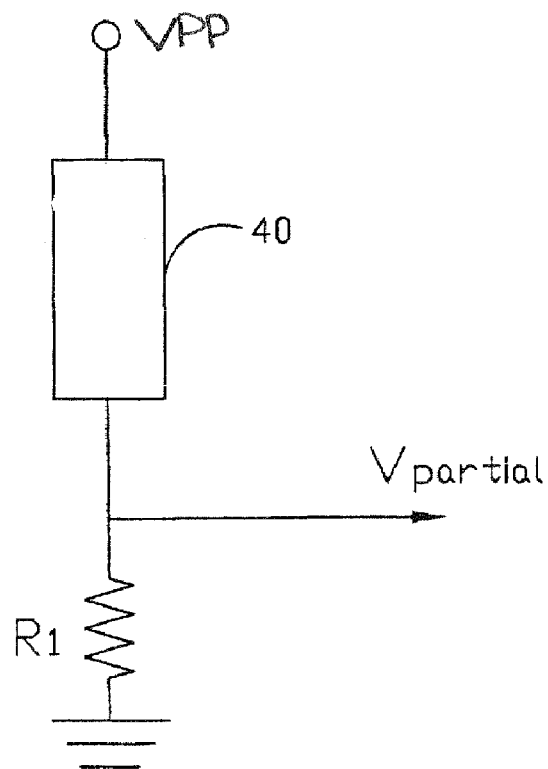
FIG. 4 is an exemplary diagram used for explaining the principle of the present biosensor.

The present invention provides a biosensor for monitoring an analyte content with a partial voltage generated therefrom. The present biosensor omits the current/voltage converter, for example the operational amplifier, and directly detects a partial voltage from the chip of the present biosensor generated by a response current caused in response to the content of the analyte of the specimen applied on the chip. In other words, the control circuit of the main detecting unit of the present invention is not provided with the current/voltage converter, such as the operational amplifier. Then, the content of the analyte is determined in accordance with the detected partial voltage. The principal of the present biosensor for determining the content of the analyte of the specimen by detecting the partial voltage from the chip generated therefrom can be explained in accordance with an exemplary diagram of FIG. 4. A chip 40 of the present biosensor is serially connected to one end of a resistor $R_1$ with the other end connected to a ground. A power source $V_{DD}$ is used to supply an applied voltage on the chip 40 to induce a response current passing through the chip 40 in response to the content of the analyte. Therefore, a partial voltage $V_{partial}$ exits between the chip 40 and the resistor $R_1$. The chip 40 has a resistance $R_S$, which is infinite when there is not any specimen applied thereon. Hence, a zero partial voltage would be detected between the chip 40 and the resistor $R_1$ when there is not any specimen applied thereon whether the chip 40 is plugged into or unplugged into the main detecting unit of the present biosensor or not. However, upon the specimen applied on the chip 40, and a power source $V_{DD}$ applied on the chip 40, the analyte of the specimen to be detected would change the resistance $R_s$, making it abruptly decreased. A time-dependent response current I is generated on the chip 40 in response to the content of the analyte, and passing through the chip 40. A time-dependent partial voltage $V_{partial}$ thus exists between the chip 40 and the resistor $R_1$, and can be represented by the formula of $V_{partial}=IR_1$, which is in proportional to the content of the analyte. The present biosensor determines the content of the analyte by directly detecting the partial voltage $V_{partial}$ caused from the chip 40. The interference of electronic parts of the present biosensor for the detection of the partial voltage $V_{partial}$ is eliminated. The discrimination of the content of the analyte of the specimen is improved.

Figure 5:
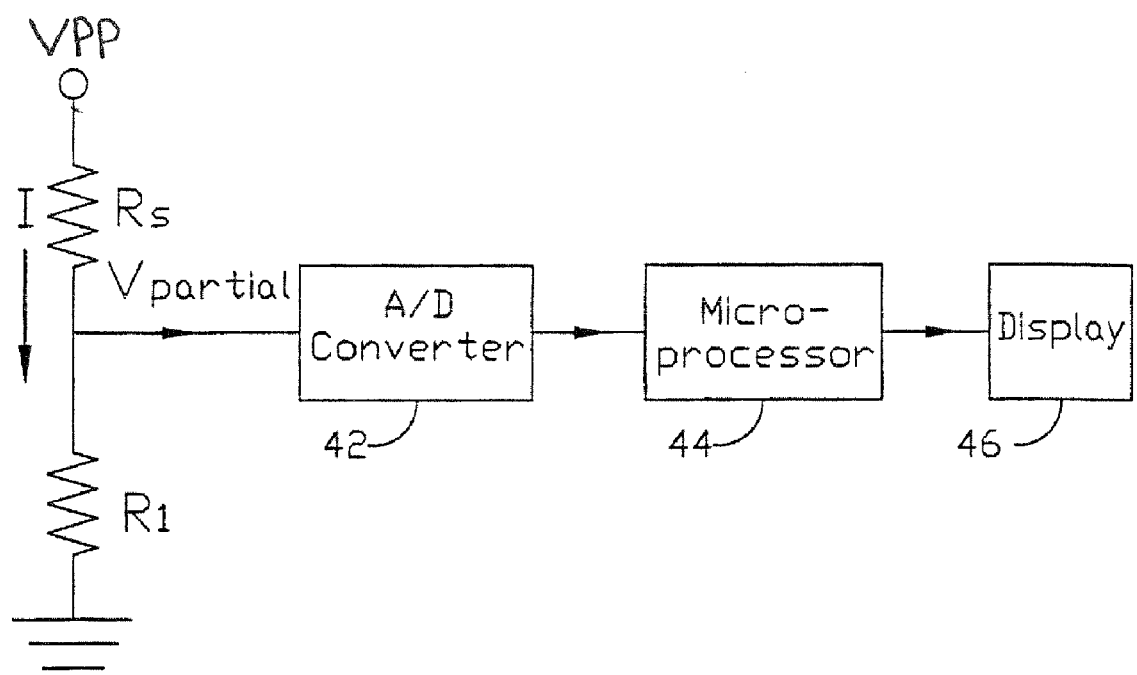
FIG. 5 is a schematic diagram of a control circuit of the present biosensor according to a preferred embodiment of the present invention.
Figure 6:
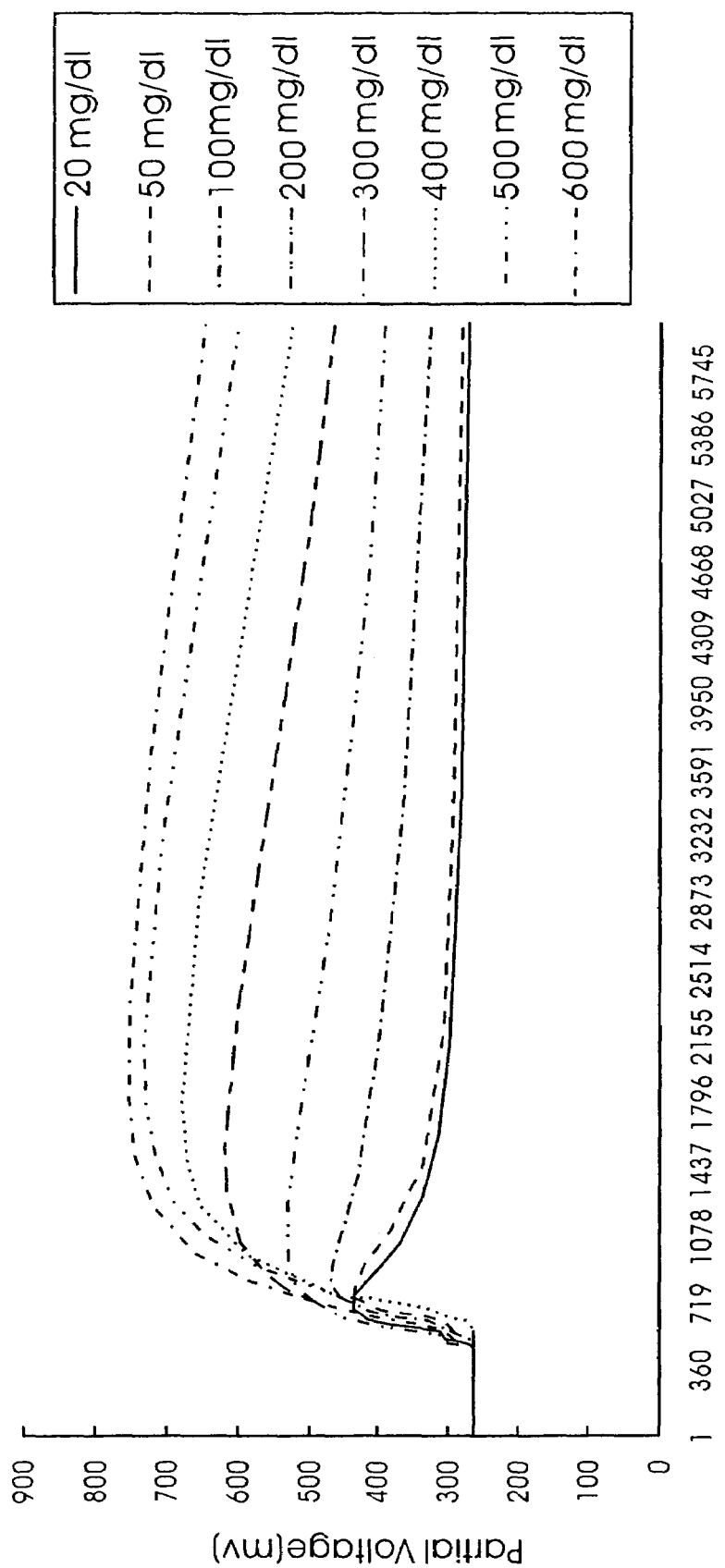
FIG. 6 is a diagram of various time-dependent partial voltage curves.

FIG. 5 is a schematic diagram of a control circuit of the present biosensor in accordance with a preferred embodiment. The control circuit of the preferred embodiment includes a power source $V_{DD}$, a chip 40 having a resistance $R_S$, a resistor $R_1$, an analog-to-digital converter 42, a microprocessor 44 and a display 46. The power source $V_{DD}$ supplies an applied voltage on the chip 40, and the chip 40 generates a time-dependent response current I in response to the content of the analyte of the specimen applied thereon upon supplying the applied voltage on the chip 40. The resistor $R_1$ has one end serially connected to the chip 40 and the other end connected to a ground. As a consequence, the time-dependent response current I passing through the chip 40 causes a time-dependent partial voltage V.sub.partial between the chip 40 and the resistor R.sub.1, which can be represented by the formula of V.sub.partial=IR.sub.1. The time-dependent partial voltage V.sub.partial constitutes a voltage-time discharge curve, for example, as shown in FIG. 6, which is a diagram of various time-dependent partial voltage curves, each of which corresponds to a blood glucose concentration, detected by the present biosensor. A peak voltage and a rising time corresponding to the peak voltage can be obtained from the respective time-dependent partial voltage curve. The peak voltage means a maximum voltage of the respective time-dependent partial voltage curve. The time-dependent partial voltage V.sub.partial is directly sent to the analog-to-digital converter 42 for being converted to a digital form under each sampling time, and then sent to the microprocessor 44 for further processing. Then, the microprocessor 44 calculates the content of the analyte in accordance with the time-voltage discharge curve formed of the time-dependent partial voltage. The analog-to-digital converter 42 also can be installed in the microprocessor 44 for receiving the time-dependent partial voltage. The microprocessor 44 can determine the content of the analyte in the following ways: For example, a mapping table of rising time versus content of the analyte can be previously established in the microprocessor 44, and a rising time can be obtained from the detected time-dependent partial voltage curve. Then, the microprocessor 44 determines the content of the analyte in accordance with the mapping table. Alternately, a mapping table of peak voltage versus content of the analyte can be previously established in the microprocessor 44, and a peak voltage can be obtained from the detected time-dependent partial voltage curve. Then, the microprocessor 44 determines the content of the analyte in accordance with the mapping table. Furthermore, a mapping table of rising time versus prescribed curve of the analyte can be previously established in the microprocessor 44, and a rising time can be obtained from the time-dependent partial voltage curve. Then, the microprocessor 44 determines the content of the analyte in accordance with the prescribed curve corresponding thereto. Moreover, a mapping table of peak voltage versus prescribed curve of the analyte can be previously established in the microprocessor 44, and a peak voltage can be obtained from the time-dependent partial voltage curve. Then, the microprocessor 44 determines the content of the analyte in accordance with the prescribed curve corresponding thereto. A reading of the content of the analyte is outputted to the display 46, for example a liquid crystal display, for shown to a patient.

In another aspect, the resistor R.sub.1 may be replaced with a variable resistor in order that the partial voltage V.sub.partial can be adjusted to be in the range acceptable by the analog-to-digital converter 42. And, the microprocessor 44 establishes a plurality of mapping tables each of which corresponding to one adjustable resistance of the variable resistor. The types of the mapping tables are the same with the above-mentioned.

The present invention directly detects a partial voltage V.sub.partial caused from the chip 40 due to the analyte of the specimen applied thereon. The electronic parts of the present biosensor are less than the conventional one, as shown in FIG. 1. Cost reduction thus can be obtained, and the power consumption can be reduced. Additionally, the present biosensor does not need to use operational amplifier means to serve as a current/voltage converter, the static current and dark current caused due to operational amplifier means are prevented when the present biosensor is standby. Therefore, a use time of a battery for supplying power to the present biosensor can be extended. In other words, the convenience for using the present biosensor is increased.

The embodiments are only used to illustrate the present invention, not intended to limit the scope thereof. Many modifications of the embodiments can be made without departing from the spirit of the present invention.

What is claimed is:

1. A biosensor capable of monitoring a content of an analyte with a partial voltage generated therefrom, the biosensor comprising:
   a chip capable of generating a time-dependent response current in response to a content of an analyte of a specimen applied thereon upon supplying an applied voltage on the chip;
   a power source capable of supplying the applied voltage on the chip; and
   a microprocessor capable of:
      receiving a time-dependent partial voltage from the chip due to the time-dependent response current;
      accessing a mapping table responsive to the time-dependent partial voltage; and
      determining the content of the analyte from the mapping table.

2. The biosensor of claim 1, further comprising an analog to digital converter capable of converting the time-dependent partial voltage to a digital form.

3. The biosensor of claim 2, further comprising a resistor with one end thereof serially connected to the chip and the other end thereof connected to a ground.

4. The biosensor of claim 3, where the resistor comprises a variable resistor.

5. The biosensor of claim 3,
   where the mapping table further comprises a mapping table of rising time versus content of the analyte;
   where a rising time is obtainable from the time-dependent partial voltage; and
   where the content of the analyte is determinable with the rising time.

6. The biosensor of claim 3,
   where the mapping table further comprises a table of peak voltage versus content of the analyte;
   where a peak voltage is obtainable from the time-dependent partial voltage; and
   where the content of the analyte is determinable from the peak voltage.

7. The biosensor of claim 3,
   where the mapping table further comprises a table of rising time versus prescribed curve of the analyte;
   where a rising time is obtainable from the time-dependent partial voltage; and
   where the content of the analyte is determinable from the rising time of a corresponding prescribed curve.

8. The biosensor of claim 3,
   where the mapping table further comprises a table of peak voltage versus prescribed curve of the analyte;
   where a peak voltage is obtainable from the time-dependent partial voltage; and
   where the content of the analyte is determinable from the prescribed curve of the analyte.

9. The biosensor of claim 3, where the analyte to be monitored depends on an enzyme of the chip.

10. The biosensor of claim 1, further comprising a resistor with one end thereof serially connected to the chip and the other end thereof connected to a ground.

11. The biosensor of claim 10, where the resistor comprises a variable resistor.

12. The biosensor of claim 10,
where the mapping table further comprises a table of rising time versus content of the analyte;
where a rising time is obtainable from the time-dependent partial voltage; and
where the content of the analyte is determinable from the rising time.

13. The biosensor of claim 10,
where the mapping table further comprises a table of peak voltage versus content of the analyte; and
where a peak voltage is obtainable from the time-dependent partial voltage; and
where the content of the analyte is determinable from the peak voltage.

14. The biosensor of claim 10,
where the mapping table further comprises a table of rising time versus prescribed curve of the analyte;
where a rising time is obtainable from the time-dependent partial voltage; and
where the content of the analyte is determinable from the rising time of a corresponding prescribed curve of the analyte.

15. The biosensor of claim 10,
where the mapping table further comprises a table of peak voltage versus prescribed curve of the analyte;
where a peak voltage is obtainable from the time-dependent partial voltage; and
where the content of the analyte is determinable from the prescribed curve of the analyte.

16. The biosensor of claim 1,
where the mapping table further comprises a table of rising time versus content of the analyte; and
where a rising time is obtainable from the time-dependent partial voltage; and
where the content of the analyte is determinable from the rising time.

17. The biosensor of claim 1,
where the mapping table further comprises a table of peak voltage versus content of the analyte; and
where a peak voltage is obtainable from the time-dependent partial voltage; and
where the content of the analyte is determinable from the peak voltage.

18. The biosensor of claim 1,
where the mapping table further comprises a table of rising time versus prescribed curve of the analyte;
where a rising time is obtainable from the time-dependent partial voltage; and
where the content of the analyte is determinable from the rising time.

19. The biosensor of claim 1,
where the mapping table further comprises a table of peak voltage versus prescribed curve of the analyte;
where a peak voltage is obtainable from the time-dependent partial voltage; and
where the content of the analyte is determinable from the prescribed curve.

20. The biosensor of claim 1, where the analyte to be monitored depends on an enzyme of the chip.

21. A method comprising:
generating a time-dependent partial voltage across a variable resistor in response to a content of an analyte of a specimen;
accessing at least one of a plurality of mapping tables responsive to the variable resistor and to the time-dependent partial voltage; and
employing the at least one of a plurality of mapping tables to determine the content of the analyte.

22. The method of claim 21, where employing the at least one of a plurality of mapping tables further comprises:
obtaining a rising time from the time-dependent partial voltage: and
determining the content of the analyte from the rising time.

23. The method of claim 21, where employing the at least one of a plurality of mapping tables further comprises:
obtaining a peak voltage from the time-dependent partial voltage; and
determining the content of the analyte from the peak voltage.

24. The method of claim 21, further comprising:
mapping a rising time versus prescribed curve of the analyte prior to the employing the at least one of a plurality of mapping tables.

25. The method of claim 21, further comprising:
mapping a peak voltage versus prescribed curve of the analyte prior to the employing the at least one of a plurality of mapping tables.

26. A sensor capable of monitoring a content of an analyte based on a partial voltage generated therefrom, comprising:
circuitry capable of generating a time-dependent partial voltage in response to the content of the analyte; and
a microprocessor capable of:
receiving the time-dependent partial voltage from the circuitry; and
determining the content of the analyte in accordance with:
(1) the time-dependent partial voltage; and
(2) a mapping table relating the time-dependent partial voltage to the content of the analyte.

27. The apparatus of claim 26, where the mapping table comprises a table of rising time versus the content of the analyte.

28. The apparatus of claim 26, where the mapping table comprises a table of peak voltage versus content of the analyte.

29. A biosensor capable of monitoring an analyte content if connected to a power source, the biosensor comprising:
a chip having applied thereon an analyte, the power source inducing a response current in the analyte based on a content of the analyte;
a microprocessor capable of:
receiving a time-dependent partial voltage resulting from the response current;
accessing at least one mapping table responsive to the receiving; and
determining the content of the analyte in accordance with the at least one mapping table.

30. The biosensor of claim 29,
where the at least one mapping table further comprises a table of rising time versus content of the analyte;
where a rising time is obtainable from the time-dependent partial voltage; and
where the content of the analyte is determinable from the at least one mapping table.

31. The biosensor of claim 29, where the microprocessor further comprises an analog to digital converter capable of converting the time-dependent partial voltage to a digital form.

32. A sensor comprising:
circuitry capable of generating a time-dependent partial voltage in response to the content of an analyte, the circuitry including a variable resistor; and
a microprocessor capable of:
receiving the time-dependent partial voltage from the circuitry due to the time-dependent partial voltage; and
determining the content of the analyte in accordance with:
(1) the time-dependent partial voltage; and
(2) one of a plurality of mapping tables corresponding to a particular resistance of the variable resistor and capable of relating the time-dependent partial voltage to the content of the analyte.

33. The apparatus of claim 32, where the mapping table comprises a table of rising time versus the content of the analyte.

34. The apparatus of claim 32, where the mapping table comprises a table of peak voltage versus content of the analyte.

35. A biosensor comprising:
means for supplying a source voltage to the biosensor, the voltage source being configured to induce a time-dependent current in the biosensor responsive to a content of an analyte;
means for measuring a time-dependent partial voltage across a resistor responsive to the time-dependent current, the resistor being coupled at a first terminal to the biosensor and being coupled at a second terminal to ground; and
means for determining the content of the analyte responsive to the time-dependent partial voltage.

36. The biosensor of claim 35 comprising
means for accessing at least one of a plurality of mapping tables responsive to the time-dependent partial voltage;
where the means for determining the content of the analyte occurs responsive to the means for accessing the at least one of the plurality of mapping tables.

37. The biosensor of claim 35 where the means for determining the content of the analyte includes:
means for measuring a rising time from the time-dependent partial voltage; and
means for determining the content of the analyte responsive to the means for measuring the rising time.

38. The biosensor of claim 35 where the means for determining the content of the analyte includes:
means for measuring a peak voltage from the time-dependent partial voltage; and
means for determining the content of the analyte from the peak voltage.

39. The biosensor of claim 35 where the means for determining the content of the analyte includes:
means for mapping a rising time versus prescribed curve of the analyte; and
means for determining the content of the analyte from the prescribed curve of the analyte.

40. The biosensor of claim 35 where the means for determining the content of the analyte includes:
means for mapping a peak voltage versus prescribed curve of the analyte; and
means for determining the content of the analyte from the prescribed curve of the analyte.

* * * * *

UNITED STATES PATENT AND TRADEMARK OFFICE
CERTIFICATE OF CORRECTION

| | | |
|---|---|---|
| PATENT NO. | : 7,347,925 B2 | Page 1 of 1 |
| APPLICATION NO. | : 10/609617 | |
| DATED | : March 25, 2008 | |
| INVENTOR(S) | : Jun-Wei Hsieh | |

It is certified that error appears in the above-identified patent and that said Letters Patent is hereby corrected as shown below:

Title Page, Item (56) column 2, line 6, please delete "12/1973" and insert -- 07/1973 --.

At column 6, line 35, please delete "mapping" after the words --comprises a--.

At column 8, line 9, please delete "voltage:" and insert --voltage;--.

Signed and Sealed this

Twenty-sixth Day of October, 2010

David J. Kappos
*Director of the United States Patent and Trademark Office*